United States Patent [19]

Kaesemeyer

[11] Patent Number: 5,543,430
[45] Date of Patent: Aug. 6, 1996

[54] METHOD AND FORMULATION OF STIMULATING NITRIC OXIDE SYNTHESIS

[76] Inventor: W. H. Kaesemeyer, 2433 McDowell St., August, Ga. 30904

[21] Appl. No.: 321,051

[22] Filed: Oct. 5, 1994

[51] Int. Cl.⁶ .................................................. A61K 31/195
[52] U.S. Cl. ........................................................ 514/565
[58] Field of Search ............................................. 514/565

[56] References Cited

U.S. PATENT DOCUMENTS

| | | | |
|---|---|---|---|
| 5,132,407 | 7/1992 | Stuehr et al. | 530/395 |
| 5,266,594 | 11/1993 | Dawson et al. | 514/560 |
| 5,273,875 | 12/1993 | Griffith et al. | 435/240 |
| 5,281,627 | 1/1994 | Griffith et al. | 514/565 |
| 5,286,739 | 2/1994 | Kilbourn et al. | 514/400 |

OTHER PUBLICATIONS

A 118: 32771 (1992).
CA 121 54642 (1994).
Anderson, Todd J. et al. *Nitric Oxide and Nitrovasodilators: Similarities, Differences and Potential Interactions.* The American College of Cardiology. vol. 24, No. 2:555–566, 1994.
Sessa, William C. *The Nitric Oxide Synthase Family of Proteins.* J Vasc. Res. 31:131–143, 1994.
Drexler M. D., Helmut et al. *Effect of L–Arginine on coronary Endothelial Function in Cardiac Transplant Recipients: Relation to Vessel Wall Morphology.* Circulation. 89, 4:1615–1623, 1994.
Kumagai, Kazuhiro, et al. *Nitric Oxide Increases Renal Blood Flow by Interacting With the Sympathetic Nervous System.* Hypertension. 24, 2:220–226, 1994.
Quyyumi, Arshed A., et al. *Effect of L–Arginine, the Substrate for Nitric Oxide, on Endothelium–Dependent Vasodilation of the Coronary Microvasculature.* Journal Am. Coll. Cardiol; Abstracts. vol. 21, No. 2:151, 1993.
Faraci, PhD., Frank, et al. *Nitric Oxide and the Cerebral Circulation.* Progress Review. 692–702, 1993.
Kitamura, Yoshihiko. *Nitric Oxide–Mediated Retinal Arteriolar and Arterial Dilation Induced by Substance P.* Investigative Ophthalmology & Visual Science. 34, 10:2859–2865, 1993.
Dinerman, Jay L. et al. *Molecular Mechanisms of Nitric Oxide Regulation: Potential Relevance to Cardiovascular Disease.* Circulation Research. 73, 2:217–222, 1993.
De Garavilla, Lawrence, et al. *Lack of Cross–Tolerance Between Nitroglycerin and Endothelium–Derived relaxing factor–mediated vasoactive agents in Spontaneously Hypertensive Rats.* European Journal of Pharmacology. 234:77–82, 1993.
Weyrich, PhD., Andrew S., et al. *The Role of L–Arginine in Ameliorating Reperfusion Injury After Myocardial Ischemia in the Cat.* Circulation. vol. 86, No. 1:279–287, 1992.
Mayhan, William G., et al. *Acetylcholine Induces Vasoconstriction in the Microcirculation of Cardiomyopathic Hamsters: Reversal by L–Arginine.* Biochemical and Biophysical Research Communications. 184, 3:1372–1377, 1992.

Smith, Russell E. A., et al. *Role of Nitric Oxide Synthesis in the Regulation of Coronary Vascular Tone in the Isolated Perfused Rabbit Heart.* Cardiovascular Research. 26:508–512, 1992.
Dinerman, J. L. et al. *Interactions Between Nitroglycerin and Endothelium in Vascular Smooth Muscle Relaxation.* The American Physiological Society. H698–H701, 1991.
Richard, V., et al. *The L–Arginine Nitric Oxide Pathway in the Canine Femoral Vascular Bed: In Vitro and In Vivo Experiments.* Fundam Clin Pharmacol. 5:777–788, 1991.
Schror, Karsten, et al. *Generation of Nitric Oxide from Organic Nitrovasodilators during Passage through the Coronary Vascular Bed and Its Role in Coronary Vasodilatoin and Nitrate Tolerance.* Blood Vessels. 28:62–66, 1991.
Bennett, Brian M., et al. *Relationship between Biotransformation of Glyceryl Trinitrate and Cyclic GMP Accuulation in Various Cultured Cells Lines.* The Journal of Pharmacology and Experimental Therapuetics. 313–323 vol. 250, No. 1, 1980.
Ignarro, PhD., Louis J., et al. *Pharmacology of Endothelium–Derived Nitric Oxide and Nitrovasodilators.* Conferences and Reviews; West J Med. 154:51–62, 1991.
Drexler, Helmut, et al. *Correction of Endothelial Dysfunciton in Coronary Microcirculation of Hypercholesterolaemic Patients by L–Arginine.* The Lancet. 338:1546–1550, 1991.
Marletta, PhD., Michael A. *Nitric Oxide, Nitrovasodilators, and L–Arginine—An Unusual Relationship.* The Western Journal of Medicine. 154, 1:107–109, 1991.
Yang, Zhihong, et al. *Endothelium–Derived Nitric Oxide in Human Arteries and Veins.* Nitric Oxide from L–arginine: a bioregultory system. 89–93, 1990.
Vedernikov, Yuri P., et al. *Endothelium–Derived Relaxing Factor is not Identical to Nitric Oxide.* Nitric Oxide from L–arginine: a bioregultory system. 373–377, 1990.
Schroder, Henning, et al. *Cross–Tolerance to L–Arginine–Dependent Guanylate Cyclase Activators in Nitrate–Tolerant LLC–PK₁ Kidney Epithelial Cells.* Pol. J. Pharmacol. Pharm. 42:259–263, 1990.
Palmer, R. M. J. et al. *L–Arginine–Induced Hypotension.* The Lancet. 696, 1990.
Gold, Michele E., 'et al. *Depletion of Arterial L–Arginine Causes Reversible Tolerance to Endothelium–Dependent Relaxation.* Biochemical and Biophysical Research Communications. 164, 2:714–721, 1989.

(List continued on next page.)

*Primary Examiner*—Paul J. Killos
*Attorney, Agent, or Firm*—Pearne, Gordon, McCoy & Granger

[57] ABSTRACT

A therapeutic mixture comprising a mixture of L-arginine and an agonist of nitric oxide synthase, namely nitroglycerin, is disclosed for the treatment of diseases related to vasoconstriction, wherein the vasoconstriction is relieved by stimulating the constitutive form of nitric oxide synthase (cNOS) to produce native nitric oxide (NO). The native NO having superior beneficial effect when compared to exogenous NO produced by a L-arginine independent pathway in terms of the ability to reduce clinical endpoints and mortality.

22 Claims, 5 Drawing Sheets

OTHER PUBLICATIONS

Palmer, D. S., R. M. J., et al. *Vascular Endothelial Cells Synthesize Nitric Oxide from L-arginine.* Nature. 333:664–666, 1988.

Flaherty, M. D., John T. *Comparison of Intravenous Nitroglycerin and Sodium Nitroprusside in Acute Myocardial Infarction.* The American Journal of Medicine. 53–60, 1983.

Bennett, Brian M., et al. *Relationship between Biotransformation of Glyderyl Trinitrate and Cyclic GMP Accumulation in Various Cultured Cell Lines.* The Journal of Pharmacology and Experimental Therapeutice. 250, 1:316–323, 1980.

*Pituitary Function: Arginine Hydrochloride.* American Hospital Form. Drug Inf. Directory. 36, 66:1418–1420, 1977.

Flaherty M. D., John T., et al. *Intravenous Nitroglycerin in Acute Myocardial Infarction.* Circulation. 51:132–139, 1975.

Feelisch, Martin et al. *Biotransformation of Organic Nitrates to Nitric Oxide by Vascular Smooth Muscle and Endothelial Cells.* Biochemical and bioPhysical Research Communications: Academic Press, Inc. vol. 180, No. 1:286–293. 1991.

*Vasodilating Agents: Nitroglycerin.* Am. Hosp. Frm. Drg. Inp. Dir. 24, 12:1033–1036. 1991.

Feelisch, Martin, et al. *Biotransformation of Organic Nitrates To Nitric Oxide By Vascular Smooth Muscle and Enothelial Cells.* Biochemical and Biophysical Research Communications. vol. 180, No. 1, pp. 286–293, 1991.

Flaherty, M. D., John T., *Comparison of Intravenous Nitroglycerin and Sodium Nitroprusside in Acute Myocardial Infarction.* The American Journal of Medicine. pp. 53–60, 1983.

Nakanishi, Katsuhiko, et al. *Intracoronary L-arginine during Reperfusion Improves Endothelial Function and Reduces Infarct Size.* The American Physiological Society, H1650–H1658, 1992.

Feelisch, M., *Biotransformation to Nitric Oxide of Organic Nitrates in Comparison to Other Nitrovasodilators.* The European Society of Cardiology. European Heart Journal, (1993), (Supplement I). pp. 123–132.

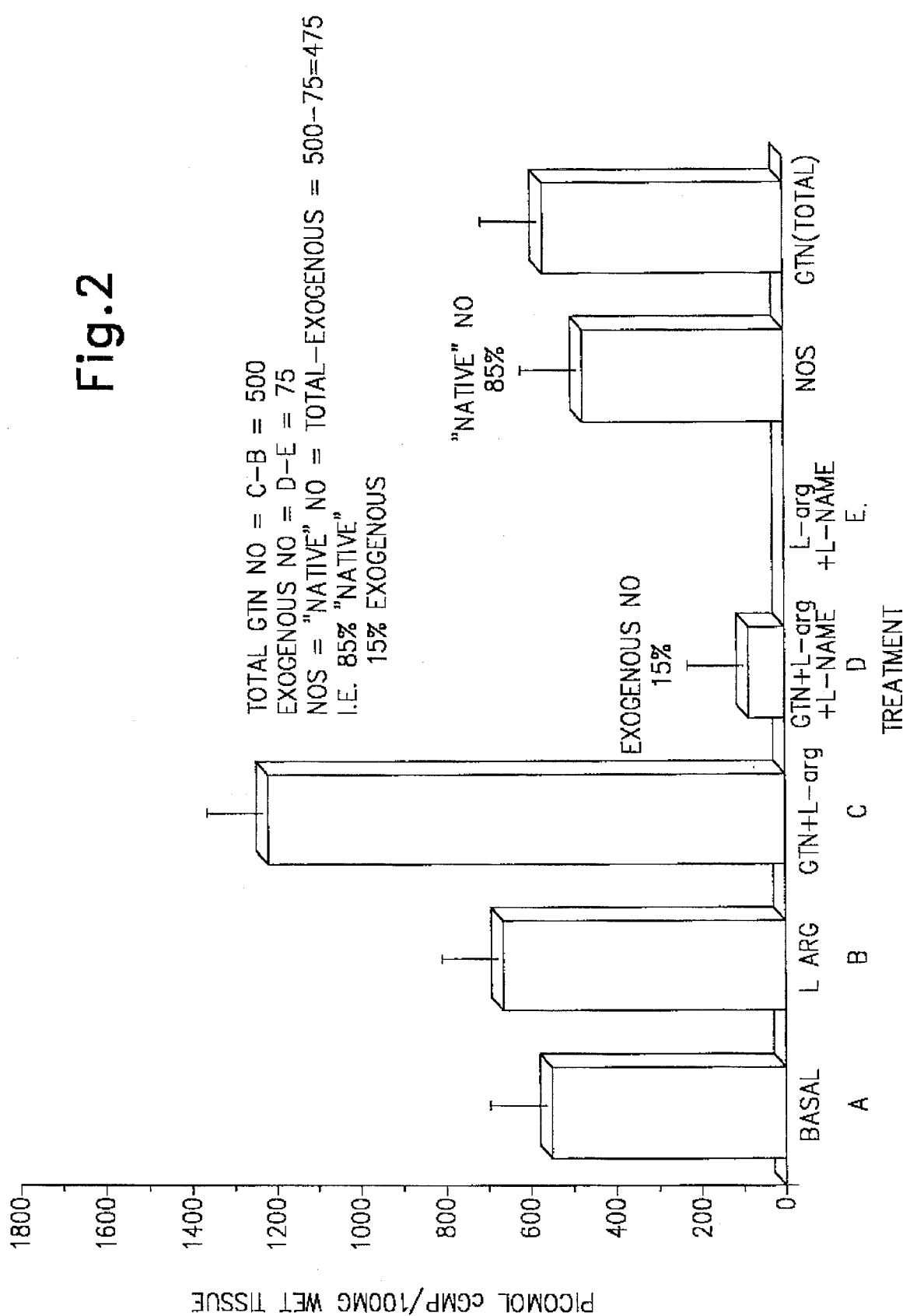

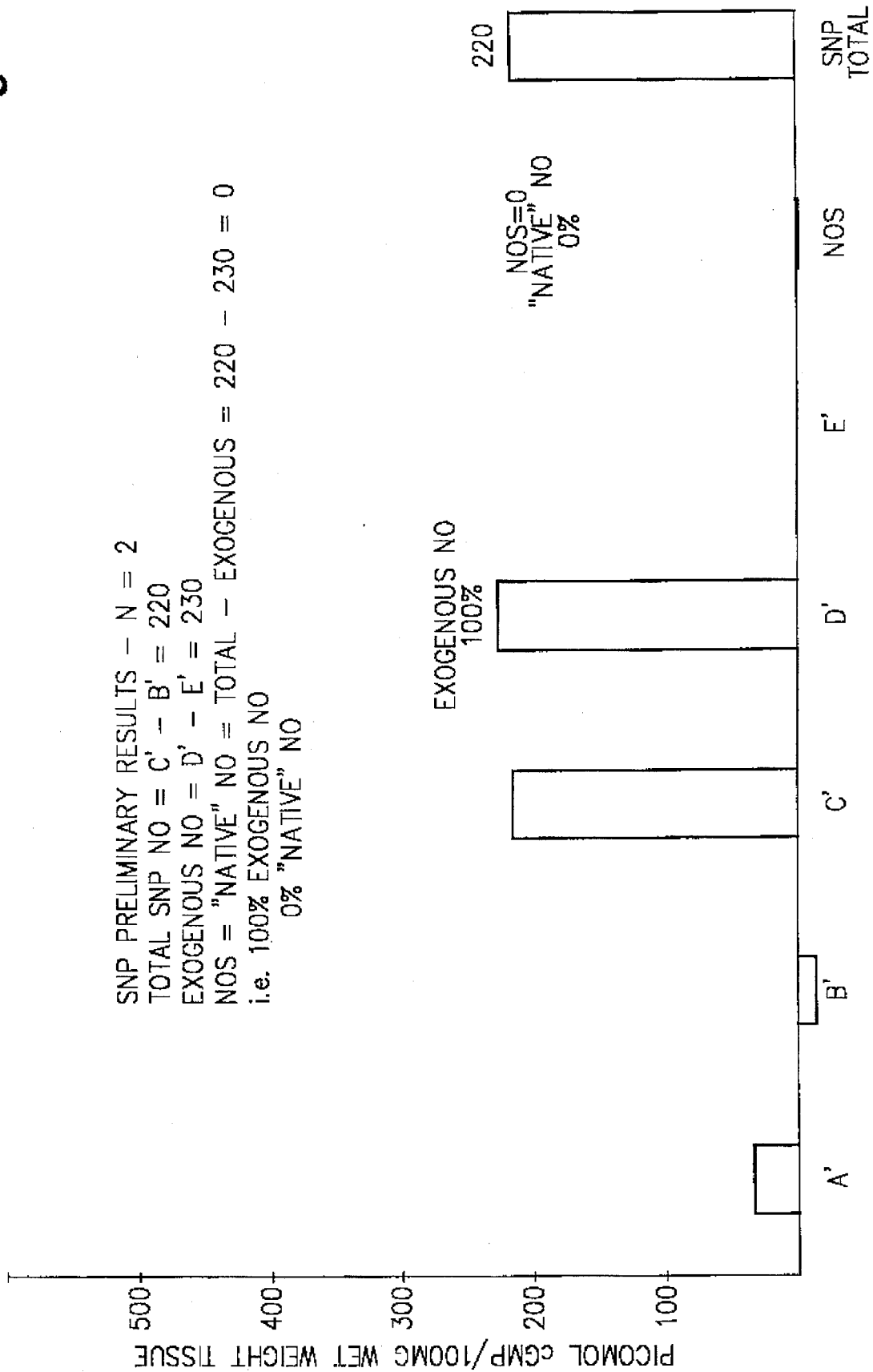

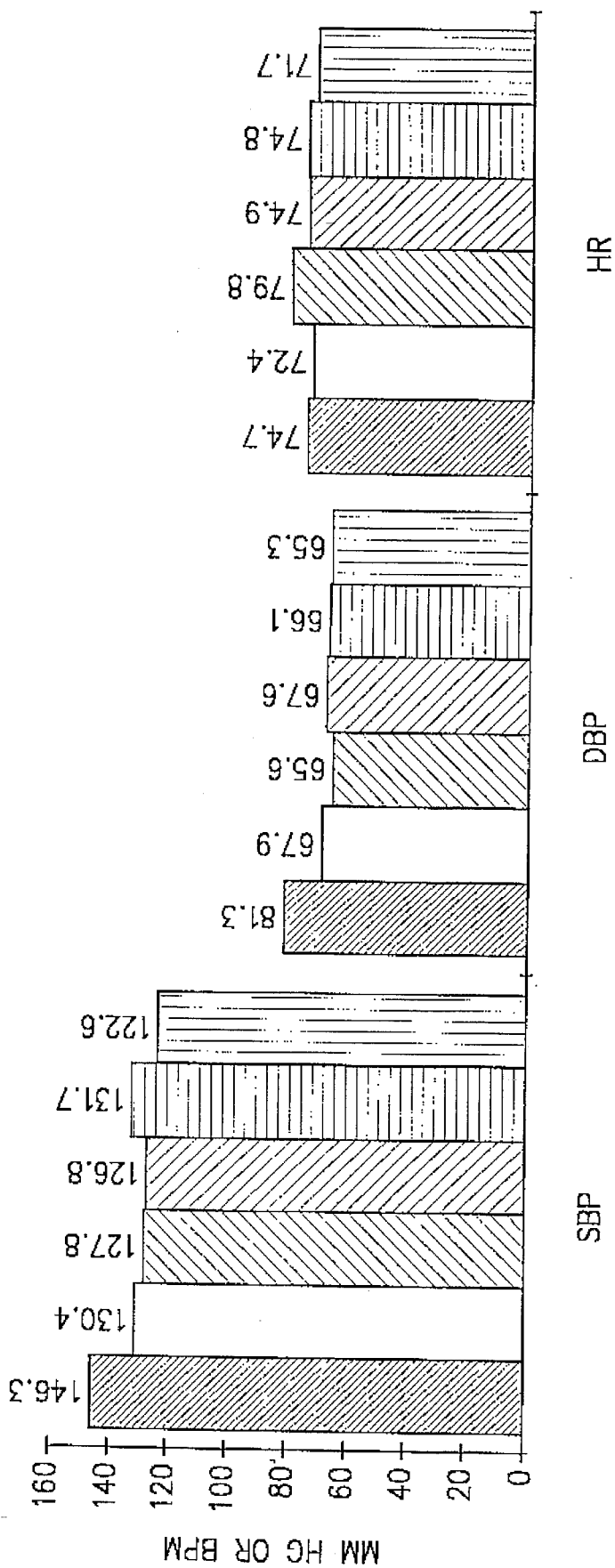

METHOD AND FORMULATION OF STIMULATING NITRIC OXIDE SYNTHESIS

BACKGROUND OF THE INVENTION

This invention relates generally to a method of treating hypertensive cardiocerebrorenovascular disease as well as non-hypertensive cardiocerebrorenovascular disease, and a unique formulation used in the treatment of these diseases and their symptoms, wherein an endogenous biological source of nitric oxide (L-arginine) and a stimulator of Nitric Oxide Synthase (NOS), particularly nitroglycerin, are mixed prior to administration to form a mixture that is useful in the treatment of nitroglycerin tolerance.

DESCRIPTION OF RELATED ART

For several decades nitroglycerin has been administered to humans as a vasodilating agent in the treatment of cardiovascular disease. Nitroglycerin or glyceryl trinitrate is an organic nitrate ester which when administered to a subject is converted biologically to nitric oxide (NO) which is a pharmacologically active metabolite. NO, for example, activates soluble guanylate cyclase in vascular smooth muscle cells which in turn increase cyclic guanosine monophosphate (cGMP) resulting in vasorelaxation, (Waldman et al., 1987, Cyclic GMP synthesis and function, Pharmacol. Rev. 39, 163.) and ultimately leads to vasodilation and a reduction in blood pressure. However, the effectiveness of nitroglycerin is greatly diminished because the recipient of therapeutic administration of nitroglycerin rapidly develops a tolerance to the beneficial effects of nitroglycerin. Therefore, onset of nitroglycerin tolerance significantly limits the therapeutic value of nitroglycerin because increased dosages have little or no effect on vasorelaxation or vasodilation. (Bogaert, M., 1991, Clinical relevance of tolerance to nitrovasodilators, J. Cardiovas. Pharmacol. 17 (Suppl. 3), S313; and Unger, P., et al., 1991, Tolerance to intravenous nitrates, J. Cardiovasc. Pharmacol. 17 (Suppl. 3), S300.) The precise mechanism of nitroglycerin tolerance is unknown. Theories explaining the tolerance include: the sulfhydryl pools necessary for the direct biotransformation of nitroglycerin into active nitric oxide are depleted by excess nitroglycerin substrate. (Boesgaard, S., et al., 1991, Nitrate tolerance: effect of thiol supplementation during prolonged nitroglycerin infusion in an in vivo rat model, J. Pharmacol. Exp. Ther. 258, 851); the activation of vascular guanylate cyclase is diminished by nitroglycerin (Henry P. J., et al., 1989, S-Nitrosothiols as vasodilators: Implications regarding tolerance to nitric-oxide-containing vasodilators, Br. J. Pharmacol. 98, 757); or that the rate of cGMP degradation may be increased during tolerance to nitroglycerin (Axelsson, K. L., et al., 1987, Nitrate tolerance from a biochemical point of view, Drugs 33, 63).

Recently, nitric oxide has also been shown to be formed enzymatically as a normal metabolite from arginine in vascular endothelium to provide an important component to the formation of endothelium-derived relaxing factor (EDRF). Macrophages and neurons have also been shown to produce nitric oxide in the body as a component of their cell killing and/or cytostatic function.

More recently it has been established that a family of enzymes called NOS form nitric oxide from L-arginine, and the nitric oxide produced is responsible for the endothelium dependent relaxation and activation of soluble guanylate cyclase, nuerotransmission in the central and peripheral nervous systems, and activated macrophage cytotoxicity (Sessa, William C., 1994, The Nitric Oxide Synthase Family of Proteins, Review, pp. 131–143,).

Nitric Oxide Synthase, occurs in many distinct isoforms which include a constitutive form (cNOS) and an inducible form (iNOS). The constitutive form is present in normal endothelial cells, neurons and some other tissues. Formation of nitric oxide by the constitutive form in endothelial cells is thought to play an important role in normal blood pressure regulation. The inducible form of nitric oxide synthase has been found to be present in activated macrophages and is induced in vascular smooth muscle cells, for example, by various cytokines and/or microbial products. It is thought that in sepsis or cytokine-induced shock, overproduction of nitric oxide by the inducible form of nitric oxide synthase plays an important role in the observed life-threatening hypotension.

As discussed above, the conversion of L-arginine into nitric oxide is enzymatically catalyzed by NOS and the resulting by-product is L-citrulline. Although it was initially described in endothelium, as discussed above, NOS activity has now been described in many cell types. Brain, endothelium, and macrophage isoforms appear to be products or different genes that have approximately 50% amino acid identity. NOS in brain and in endothelium have very similar properties, the major differences being that brain NOS is cytosolic and the endothelial enzyme is mainly a membrane-associated protein.

Functionally, the constitutive form of Nitric Oxide Synthase (cNOS), which is the predominant synthase present in brain and endothelium, may be active under basal conditions and can be further stimulated by increases in intracellular calcium that occur in response to receptor-mediated agonists or calcium ionophores. cNOS appears to be the "physiological" form of the enzyme and plays a role in a diverse group of biologic processes. In vitro studies suggest that the activity of nitric oxide synthase can be regulated in a negative feedback manner by nitric oxide itself. In the cardiocerebrorenovascular circulation, the primary target for constitutively produced nitric oxide is soluble guanylate cyclase located in vascular smooth muscle, the myocardium (myocytes) and coronary vascular smooth muscle.

In the presence of normal substrate, nitric oxide is made preferentially by nitric oxide synthase. However, in the absence of L-arginine, brain nitric oxide synthase is thought to generate the free radicals superoxide and hydrogen peroxide. This property of nitric oxide synthase has potential major implications for neurotoxicity and pathophysiological conditions such as ischemia.

In contrast, to the constitutive form of the enzyme, the inducible, calcium-independent form was initially only described in macrophages. It is now known that induction of nitric oxide synthase can occur in response to appropriate stimuli in many other cell types. This includes both cells that normally do not express a constitutive form of nitric oxide synthase, such as vascular smooth muscle cells, as well as cells such as those of the myocardium (Levine B, et al., 1990, Elevated circulating levels of tumor necrosis factor in severe chronic heart failure. N Engl J med. 323:236–241.) that express considerable levels of the constitutive isoform.

iNOS exhibits negligible activity under basal conditions, but in response to factors such as lipopolysaccharide and certain cytokines, expression occurs over a period of hours. The induced form of the enzyme produces much greater amounts of NO than the constitutive form, and induced NOS appears to be the "pathophysiological" form of the enzyme because high concentrations of NO produced by iNOS can be toxic to cells. Induction of iNOS can be inhibited-by glucocorticoids and some cytokines. Relatively little is known about postranscriptional regulation of iNOS. Cytotoxic effects of NO are probably largely independent of guanylate cyclase and cyclic GMP formation.

Most of the research in the area has focused on inhibitors of iNOS stimulation using various derivatives of L-arginine. However little research has been done on the stimulation of cNOS and its effect on nitroglycerin tolerance. Nitroglycerin tolerance has continued to frustrate the health care community because there is to date no effective way to stimulate physiological NO production above the tolerance or resistance floor of nitroglycerin so as to maintain the beneficial effect of the administration of nitroglycerin for prolonged periods.

An effective method of treating hypertensive cardiocerebrorenovascular diseases and symptoms as well as non-hypertensive cardiocerebrorenovascular diseases and symptoms so as to overcome the resistance-tolerance floor of nitroglycerin is needed in the art.

SUMMARY OF THE INVENTION

The term "subject" is used herein to mean any mammal, including humans, where nitric oxide formation from arginine occurs. The methods herein for use on subjects contemplate prophylactic use as well as curative use in therapy of an existing condition. The term "native NO" as used herein refers to the nitric oxide that is produced through the biotransformation of L-arginine or the L-arginine dependent pathway. The term endpoints as used herein refers to clinical events encountered in the course of treating cardiovascular disease, up to and including death (mortality)

It is an object of this invention to treat pharmacological tolerance to nitroglycerin.

It is another object of this invention to provide a method of preventing, treating, arresting, or ameliorating disease conditions which are benefitted by the biotransformation of L-arginine into endogenous nitric oxide or "native" nitric oxide.

It is another object of this invention is to provide a formulation that has a combined arterial and venodilatory effect.

It is another object of this invention to ameliorate or avoid tachycardia and prevent or treat ischemia.

It is another object of this invention to premix L-arginine and nitroglycerin to achieve a synergistic effect to treat nitroglycerin tolerance by increasing or maximizing the ability of nitroglycerin to produce "native" nitric oxide, and reduce clinical endpoints to include mortality.

It is another object of this invention to prevent reperfusion injury in subjects who have had abrupt restoration of blood flow.

It is another object of this invention to use the combination or mixture formed to reduce the dosage requirements of L-arginine and the corresponding deleterious consequences of volume overload.

It is a further object of this invention to provide a mixture of nitroglycerin and L-arginine for the treatment of hypertension, hypertensive heart disease; coronary heart disease, including angina, myocardial infarction, and sudden death; and a wide range of cardiovascular disease (heart failure, stroke, and peripheral vascular diseases), and renovascular ischemia/hypertension.

These and other objects of this invention are provided by one or more of the embodiments provided below.

In one embodiment of the invention, therapeutically effective amounts of L-arginine and a cNOS agonist are mixed together prior to administration to a subject.

In another embodiment of the invention, therapeutically effective amounts of L-arginine and nitroglycerin are combined at a physiologically acceptable pH prior to administration.

In another embodiment a method for treating hypertension in a subject by vasodilation or vasorelaxation comprises: selecting a hypertensive subject; administering to said subject an anti-hypertensive formulation comprising a mixture of a venous dilator; and an arterial dilator; obtaining periodic blood pressure measurements of the subject; and; continuing administration of the formulation until a desirable blood pressure or therapeutic effect is detected in the subject. A desirable blood pressure in a hypertensive subject should ultimately be within the following ranges: systolic preferably in the range of 95–180 mmHg, more preferably in the range of 105–165 mmHg, and even more preferably in the range of 120 to 140 mmHg; and diastolic preferably in the range of 55–115 mmHg, more preferably in the range of 65–100 mmHg, and even more preferably in the range of 70 to 90 mmHg, and most preferably 75–85 mmHg. Under no circumstances should the systolic be permitted to go below 95 mmHg.

Another embodiment is a method for preventing or treating cardiovascular disease in a non-hypertensive subject by vasodilation or vasorelaxation comprising: selecting a subject; administering to said subject a formulation comprising a mixture of a venous dilator and an arterial dilator wherein the venous dilator is a combined non-endothelium and endothelium dependent source of nitric oxide (i.e. nitroglycerin) and said arterial dilator is an endothelium dependent source of nitric oxide (L-arginine); obtaining periodic measurements of vasorelaxation on the subject and; continuing administration of the formulation until a desirable state of vasorelaxation or desirable therapeutic effect is detected on the subject. A desirable state-of vasorelaxation is for example a lowering of the systolic by about 20 mmHg and a lowering of the diastolic by about 10 mmHg. Under no circumstances should the systolic be lowered less than 95 mmHg.

Yet another embodiment is a method for treating hypertension in a subject by vasodilation comprising: selecting a hypertensive subject; administering to said subject an anti-hypertensive formulation comprising a mixture of L-arginine and nitroglycerin; obtaining periodic blood pressure measurements on the subject; and; continuing administration of the anti-hypertensive formulation until a desirable blood pressure is detected in the subject.

Yet another embodiment is a method for stimulating cNOS in a subject which comprises: selecting a subject; administering to said subject a formulation comprising a mixture of L-arginine and nitroglycerin, so as to maximize "native" NO production in order to treat tolerance and reduce endpoints to include mortality.

BRIEF DESCRIPTION OF THE DRAWINGS

FIG. 2 is a bar graph illustrating the cNOS stimulating effect of combined administration of L-arginine and nitroglycerin on rat aorta.

FIG. 3 is a bar graph illustrating the absence of cNOS stimulating effect of combined administration of L-arginine and SNP on rat aorta.

FIG. 4 is a human dose study which demonstrates the absence of tachycardia during administration of the herein described formulation.

DETAILED DESCRIPTION OF THE PREFERRED EMBODIMENTS

It has been discovered that combining L-arginine with nitroglycerin prior to administration overcomes the resistance or tolerance level normally established when administering nitroglycerin alone. It is believed that NOS may be stimulated by nitroglycerin and that premixing with L-arginine has a synergistic beneficial effect that may be due to a complex or coordinate formation between nitroglycerin and L-arginine. Excess L-arginine provides additional substrate for the stimulated nitric oxide synthase which catalyzes the biotransformation of L-arginine into nitric oxide.

Such stimulation of NOS in the presence of excess L-arginine may be used to prevent, treat, arrest, or ameliorate any disease or condition which may be positively affected by NO production. Such conditions include hypertensive cardiocerebrorenovascular diseases and symptoms as well as non-hypertensive cardiocerebrorenovascular diseases. The mixture is particularly useful for subjects in need of native NO production. Application of such a mixture is beneficial for: (1) Chronic stable angina; (2) Unstable angina; (3) Acute myocardial infarction; (4) Hibernating myocardium; (5) Stunned myocardium; (6) Limitation of ventricular remodeling in post myocardial infarction and subsequent risk of congestive heart failure; (7) Prophylaxis of recurrent myocardial infarction; (8) Prevention of sudden death following myocardial infarction; (9) Vasospastic angina; (10) Congestive heart failure-systolic-seen in association with 1–6 above; (11) Congestive heart failure-diastolic-seen in association with 1–10 above and 12–15 below; (12) Microvascular angina seen in association with 1–11 above and 15 and 16 below; (13) Silent ischemia seen in association with 1–12 above and 15 and 16 below; (14) Reduction of ventricular ectopic activity seen in association with 1–13 above and 15 below; (15) Any or all of the above 1–14 states of ischemic myocardium associated with hypertensive heart disease and impaired coronary vasodilator reserve; (16) control of blood pressure in the treatment of hypertensive crisis, perioperative hypertension, uncomplicated essential hypertension and secondary hypertension; (17) Regression of left ventricular hypertrophy seen in association with 15 and 16 above; (18) Prevention and or regression of epicardial coronary atherosclerosis seen in 1–17 above; (19) Prevention of restenosis post angioplasty; (20) Prevention and/or amelioration of free radical mediated reperfusion injury in association with 1–19 above; (21) Use of the combination in the prevention of myocardial injury during cardioplegic arrest during coronary bypass or other open heart surgery i.e. use of the combination as a cardioplegic solution; (22) Post transplant cardiomyopathy; (23) Renovascular ischemia; (24) Cerebrovascular ischemia (Transient Ischemic Attack (TIA) and stroke).

Figure 1A:
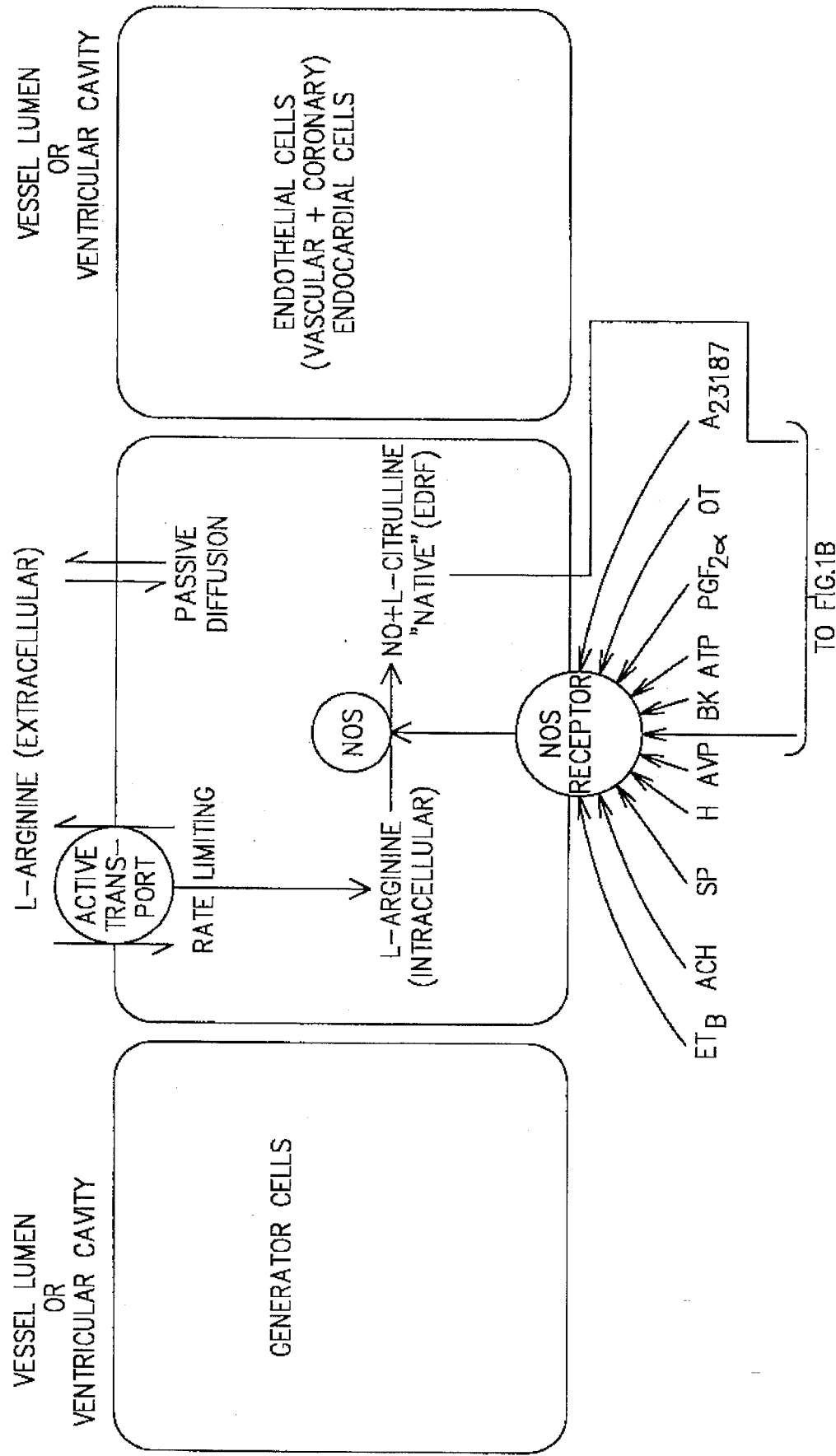
FIG. 1A is the top portion of a schematic representation of the proposed L-arginine dependent and independent pathways.
Figure 1B:
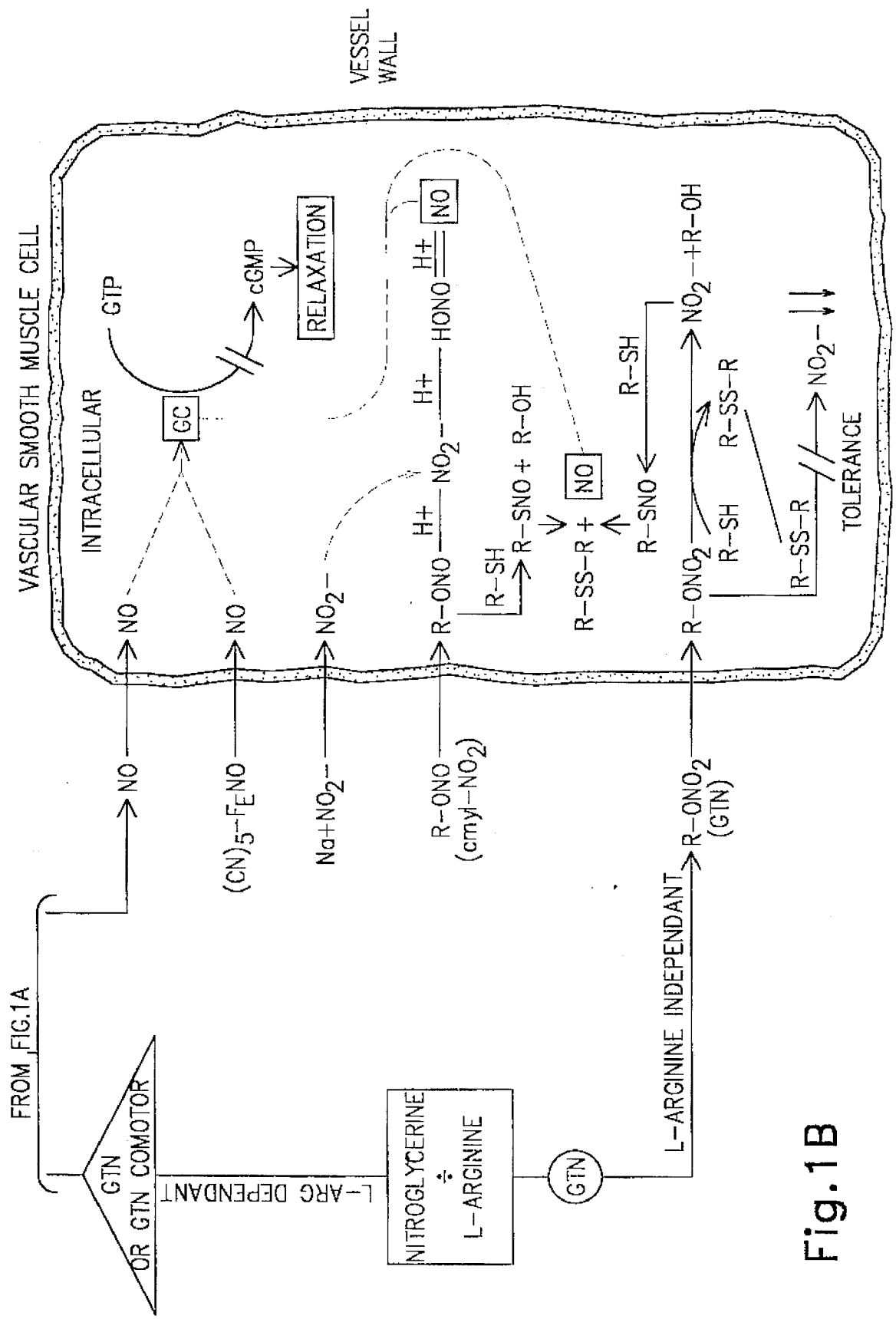
FIG. 1B is the bottom portion flowing from FIG. 1A of a schematic representation of the proposed L-arginine dependent and independent pathways.

FIG. 1A and FIG. 1B illustrate a schematic representation of the proposed mechanism of action elicited by nitrovasodilators on both a generator cell and a target cell and their interrelationship. It appears that nitroglycerin or glyceryl trinitrate's (GTN) mechanism of action is both L-arginine dependent and L-arginine independent and this implication has far reaching effects regarding the development and treatment of nitroglycerin tolerance and reducing clinical endpoints and mortality. A type of generator cell is an endothelial cell, but may also be an endocardial cell or a coronary endothelial cell; and a corresponding type of target cell is a vascular smooth muscle cell, but may also be a myocardial cell (myocyte). Vascular smooth muscle cells are located mainly in the veins, arteries, and coronary arteries. The following discussion will focus on smooth muscle and myocyte relaxation stimulated by nitrovasodilators wherein the nitric oxide synthase is cNOS, the constitutive form of nitric oxide synthase, the generator cells are endothelial cells and the target cells are vascular smooth muscle cells. This illustration is not intended to imply any cellular relationship between the various sites of action, but rather meant to illustrate their functional relationship.

As shown in FIGS. 1A and 1B the production of NO may result from a variety of sources and mechanisms which are discussed in detail in Ignarro, (Louis J. PhD., 1991, Pharmacology of Endothelium-Derived Nitric Oxide and Nitrovasodilators, The Western Journal of Medicine, pp.51–62.) which is incorporated herein in its entirety by reference. In the L-arginine independent or non-endothelium dependent pathway the activation of Guanylate Cyclase (GC) by Nitric Oxide (NO) depends on the type of nitrovasodilator used. Inorganic Nitrite ($NO_2-$) is charged and only limited amounts can permeate the cell, but intracellular nitrite can be converted to NO. Lipophilic organic nitrate esters (R—OH) are converted into NO by acidic thiol (R—SH) facilitated reactions. S-Nitrosothiols (R—SNO) are labile intermediates that decompose spontaneously and produce NO. It is thought that one of the mechanisms by which thiols potentiate the action of nitroglycerin and reverse to some degree tolerance to nitroglycerin is through the direct reaction between the thiol (R—SH) and nitroglycerin (GTN) to form the labile intermediate S-Nitrosothiol (R—SNO), which decompose as described above (R—SH+GTN→R—SNO is not shown in either FIG. 1A or FIG. 1B. A nonenzymatic formation of exogenous NO is thought to occur with thiol sources such as cysteine, dithiothreitol, N-acetylcysteine, mercaptosuccinic acid, thiosalicylic acid, and methylthiosalicylic acid. Nitrates such as isosorbide dinitrate, and isosorbide 5' mononitrate also can be used to produce NO since they are simply commercially available intermediates to the known L-arginine independent pathway. Nitroprusside (($CN)_5$—FeNO) forms NO upon breakdown and is not thiol dependent. GTP is guanosine triphosphate; HONO is nitrous acid; Meth. Blue is Methylene Blue; R—ONO is organic nitrite esters; and R—SS—R represents a disulfide. In the L-arginine independent pathway the glyceryl trinitrate (GTN) reaction is represented by R—$ONO_2$ and are thought to need a certain pool of thiols, such as a sulfhydryl containing enzyme, to generate NO and it was formerly thought that intracellular thiol deficiency results in tolerance to the pharmacological actions of nitroglycerin. This however does not account for the tolerance because exogenous dose dependent thiols do not result in reversal of nitroglycerin tolerance (Fung H. L., 1988, Journal of Pharmacology and experimental Therapeutics. 245:2,524–30.) but may exert beneficial effect as independent donors of NO, versus facilitate spontaneous release of nitric oxide. (Munzel T., M.D., et al., 1994, What Causes Nitroglycerin Tolerance? Clinical Cardiology. 20 No. 9:40–47.)

However, it is hypothesized for the first time here that the tolerance to nitroglycerin may involve a secondary pathway, or indeed, this "secondary pathway" may be the primary pathway. This "secondary pathway" is the L-arginine dependent pathway or endothelium dependent pathway shown in FIGS. 1A and 1B. As seen in FIG. 1A, the generator cell is known to have several receptor mediated agonists such as Endothelium B receptor ($ET_B$); acetylcholine (Ach); substance P (SP), Histamine (H); arginine vasopressin (AVP); bradykinin (BK); Adenosine Triphosphate (ATP); Prostaglandin $F_{2a}$ ($F_{2a}$); Oxytocin, (OT); and the calcium ionophore (A23187) which stimulate the production of NOS. However, until now it has not been speculated that nitroglycerin may serve the dual role of agonist for NOS, and pro-drug for the sulfhydryl mediated L-arginine independent pathway.

Previously it was thought that nitroglycerin had no effect on the biotransformation of L-arginine into "native" nitric oxide, but it is now believed that nitroglycerin or a nitroglycerin complex or coordinate (GTN complex in FIG. 1B) with L-arginine has a stimulating effect on cNOS. The mechanism is not well understood but it appears the novel combination of nitroglycerin and L-arginine prior to administration may have a heretofore unexpected synergistic effect on cNOS stimulation which may be due in part to a novel complex formulation that serves as a delivery system of unprocessed nitroglycerin. On the other hand the stimulation of cNOS may be a result of cNOS having a unique receptor site for the complex or nitroglycerin being in a state of disassociation equilibrium with L-arginine. Administering the two in combination also provides adequate substrate for cNOS processing of L-arginine since the L-arginine will be added in excess.

There appears to be some complex or coordinate forming between L-arginine and nitroglycerin when the two are mixed. This is shown in Table I, wherein the coordinate was studied using a Bruker 300 MHz NMR. The samples studied consisted of the following: Sample A, a concentrated standard (100 mg L-Arg in 0.5 ml $D_2O$); Sample B, a concentrated mixture (100 mg L-Arg plus one tablet of nitrostat in 0.5 ml $D_2O$); Sample C, a diluted standard (1 drop of sample A in 1.0 ml $D_2O$); and Sample D, a diluted mixture (13 mg L-Arg plus 3 tablets of nitrostat in 1 ml $D_2O$). These samples were compared and computer combined to determine whether a complex had formed. The addition of nitroglycerin to L-arginine resulted in a change in the chemical shifts for L-arginine multiplet a $\partial 1.9$ and triplet at $\partial 3.2$, the most readily studied signals. This change is shown in Table I

TABLE I

| | Signal Frequency | |
|---|---|---|
| sample C(Hz) | sample D(Hz) | change |
| Analysis of $\partial 3.2$ signal | | |
| 979.032 | 980.119 | 1.087 Hz |
| 972.107 | 973.281 | 1.174 Hz |
| 965.272 | 966.364 | 1.092 Hz |
| Analysis of $\partial 1.9$ signal | | |
| 582.392 | 584.513 | 2.121 Hz |
| 575.108 | 577.287 | 2.179 Hz |
| 573.365 | 575.607 | 2.242 Hz |
| 567.231 | 569.348 | 2.117 Hz |
| 565.698 | 568.118 | 2.420 Hz |
| 559.425 | 561.673 | 2.248 Hz |

The change in proton chemical shifts in L-arginine in the presence of nitroglycerin is a strong indicator that a complex of the substances is forming in solution to form an intermediate different from the two independent substances. This is further supported by the fact that the shift was not concentration dependent. Thus it may be fairly concluded that L-arginine and nitroglycerin do not act independently in solution but rather, are somehow involved in the formation of a complex which changes the chemical environment of the L-arginine protons and which can be detected using high resolution NMR spectroscopy. This may explain the unique beneficial NO delivery system which overcomes the resistance-tolerance threshold previously seen in the administration of nitroglycerin alone. However, the beneficial effect may merely result from the simultaneous administration of L-arginine and a cNOS stimulator.

Combining L-arginine and nitroglycerin may also result in a combined arterial and venous dilatory effect. Used alone nitroglycerin is principally a venodilator and causes rapid increase in heart beat due to its venous pooling, while L-arginine on the other hand when used alone is principally an arterial dilator. Therefore, combining the two results in balanced arterial and venodilatory effect which counter balances the tendencies of one or the other to produce tachycardia which is adverse to ischemia in an evolving myocardial infarction. This is suggested by preliminary data in dog studies and is most notable in the data shown in Table II. The data in Table II was generated by administering L-Arginine at 5 cc per minute wherein the L-arginine was at 10% w/v (g/ml) and the nitroglycerin was administered at 3.38 µg/kg/minute by Intravenous (IV) administration over a five minute period. The dog was a beagle that weighed 13.6 kg. When administered in combination, the relative concentrations and dosages remained the same. BP is Blood Pressure (systolic/diastolic in mmHg); MAP is Mean Arterial Pressure (mmHg); CO is Cardiac Output (liters/min.); TPVR is Total Peripheral Vascular Resistance (dynes*sec./ $cm^3$); $\Delta$TPVR is the change in Total Peripheral Vascular Resistance (%); and HR is Heart Rate (bpm).

TABLE II

| | Canine Study | | | | | |
|---|---|---|---|---|---|---|
| Agent | BP | MAP | CO | (TPVR) | HR | $\Delta$TPVR |
| Before L-Arginine | 130/75 | 93.3 | 1.44 | (64.8) | 105 | |
| | | | | | | 31.6% |
| After | 105/55 | 71.7 | 1.62 | (44.3) | 102 | |
| Before Nitroglycerin | 105/60 | 75.0 | 1.63 | (46.0) | 104 | |
| | | | | | | 24.5% |
| After | 70/40 | 50.0 | 1.44 | (34.7) | 105 | |
| Before Nitro- glycerin + L-Arginine | 105/60 | 75.0 | 1.56 | (48.1) | 102 | |
| | | | | | | 16.8% |
| After | 70/40 | 50.0 | 1.60 | (31.3) | 98 | |

It can be seen from looking at The effect on CO or Cardiac Output that after administration of the L-arginine alone an increase in cardiac output is due to the effect of L-arginine as principally an arterial dilator; and the decrease in cardiac output seen with nitroglycerin alone is principally due to a venous dilatory effect; while the combination produces a substantially balanced arterial and venous dilatory effect (a change in cardiac output of only 0.04 (1.60–1.56)). Hence, the absence of a tendency towards tachycardia (i.e. no evidence of baroreceptor reflex activation).

Another mechanism of benefit from the combination relates to the fact that used alone nitroglycerin is of only minimal benefit in limiting reperfusion injury with patients who have had recent heart attacks and abrupt restoration of blood flow. The same thing is seen in patients who are undergoing re-establishment of blood flow after coronary bypass operations coming off the bypass pump. This form of reperfusion injury is thought to be mediated by free radical generation upon reperfusion and preliminary data especially in cats shows that L-arginine administered alone limits free radical production. (Weyrich, A. S., PhD., et al., 1992, The Role of L-Arginine in Ameliorating Reperfusion Injury After Myocardial Ischemia in the Cat. Circulation. 86:279–288.) Therefore, the combination would be likely to limit reperfusion injury relative to nitroglycerin used alone.

Another benefit of the use of the combination relative to each used alone relates to the fact that the volunteer studies thus far with 1-arginine alone reveal it to be a weak vasodilator in terms of dosage requirements. (600 cc/hr as reported by Nakaki T., et al., 1990, L-arginine Induced Hyportension. The Lancet, p. 696). Patients who have unstable coronary syndromes and myocardial infarction with or without the complication of congestive heart failure are prone to volume overload with administration of IV fluids. Therefore by combining nitroglycerin with L-arginine one could limit remarkably the total L-arginine dosage requirement and thereby the risk for developing congestive heart failure. This might also be of importance in patients who have compromised renal function and are prone to acidosis and renal failure with large volumes of L-arginine.

The principle combination to be employed will be a mixture that involves therapuetic concentrations of L-arginine and nitroglycerin in water. Any pharmaceutical grade L-arginine will be sufficient and should be diluted preferably to 2.5–60% w/v (g/ml), more preferably to 5–45% w/v (g/ml), even more preferably between 7.5–30% w/v (g/ml), even more preferably to 10–15% w/v (g/ml), and most preferably 10% w/v (g/ml) L-arginine. The typical doses anticipated will be 30 grams of L-arginine in sterile water (Total Volume 300 cc). The L-arginine is anticipated eventually to be approximately 10:1 to about 25:1 of the hydrochloride salt: L-arginine as a base, and even more preferably 15:1 to about 20:1 hydrochloride salt to base, and most preferably 15:1 hydrochloride salt to base. In this example 28 to 29 grams will be the hydrochloride salt and 1 to 2 grams of L-arginine will be base. It is anticipated that the nitroglycerin to be combined with L-arginine will have a concentration dependent on the mass of the subject in kg and dosage time preferably in the range of 0.1 µg/kg/minute to about 5 µg/kg/minute, more preferably in the range of 0.2 µg/kg/minute to about 4 µg/kg/minute, even more preferably in the range of 0.5 µg/kg/minute to about 3 µg/kg/minute, even more preferably in the range of 0.75 µg/kg/minute to about 2 µg/kg/minute, and most preferably about 1 µg/kg/minute. Therefore depending on the IV volume, the administration time, and the weight of the subject nitroglycerin will be added in an amount sufficient to obtain the desired range (i.e. 1 µg/kg/minute). If a transdermal system is used the delivery of nitroglycerin should preferably be between 0.2 mg/hr and 1 mg/hr, more preferably between 0.3 mg/hr and 0.8 mg/hr, and even more preferably between 0.4 mg/hr and 0.6 mg/hr. It is anticipated that the package will contain freeze dried L-arginine in a glass bottle to which the nitroglycerin and sterile water would be added in such as fashion as to have 30 grams of L-arginine and 1 to 960 milligrams of nitroglycerin all diluted to a total volume with sterile water of 300 cc. Alternatively, nitroglycerin, L-arginine, and water can be added in sterilized glass bottles and adjusted to a physiological pH. The pH on reconstitution in water should preferably be in the range of approximately 5–8, more preferably in the range of 6–7.5, even more preferably in the range of 7 to 7.5, and even more preferably approximately 7.4 which is physiologic in order to avoid the present problem that is present in those solutions that require the pH limitation of 5.6 to avoid bacteriologic overgrowth on periods of prolong standing when shipped in solution.

The dose of nitroglycerin might vary according to future studies on the effect of the combination ratio on heart rate. In addition even though the discussion focuses on intravenous administration, buccal, intracoronary, intramuscular, topical, intranasal, rectal, sublingual, oral, subcutaneous, or patch administration forms alone or in combination apply as well. Because of their compatibility, the combination of L-arginine and nitroglycerin in patch may be the most common use as is the case presently for the use of nitroglycerin alone in patch form. The feasibility of patch technology is supported by solubility test of L-arginine in Tridil™. Solubility test demonstrated the following: without the addition of water, approximately 170 mg of L-arginine will dissolve in 1.0 ml of Tridil™ (5 mg of nitroglycerin/ml); a clear colorless mixture was obtained when 2500 mg of L-arginine hydrochloride, 1.0 ml of Tridil™, and 2.8 ml of deionized water were combined at 30° C. with gentle swirling and then cooled to ambient temperature (approximately 24° C.); and a very thick, yet pourable, slurry was obtained when 2500 mg of L-arginine, 1 ml of Tridil™ and only 0.5 ml of deionized water were combined. These results suggest that L-arginine and Tridil™ have a great degree of solubility compatibility and therefore could easily be incorporated into the current patch administration technology.

The following illustrate the above described mechanism of action and treatment of cardiocerebrorenovascular diseases:

EXAMPLE 1

It was recently discovered that dogs treated to a floor of nitroglycerin effect could be made further responsive by the co-administration of nitroglycerin and L-arginine in water in a manner similar to that commonly seen clinically with the addition of sodium nitroprusside (SNP) to nitroglycerin; however, when compared to SNP, L-arginine combined with nitroglycerin had much more favorable hemodynamic effects. Compared to SNP, vascular resistance was reduced by 50%, cardiac output doubled, and contractility increased. This led to the hypothesis that the combination of L-arginine and nitroglycerine was generating EDRF as opposed to SNP which is known to produce nitric oxide in a direct fashion.

Since there is still debate whether EDRF is identical to nitric oxide it was hypothesized that EDRF not being identical to NO would account for the difference in hemodynamic effect. To account for the extra EDRF it was hypothesized that nitroglycerin in addition to being a pro-drug for nitric oxide was also an agonist to cNOS activation and that L-arginine rate limitations in the canine model could be explained by a supply-demand mismatch in L-arginine uptake particularly in disease state such as hypertension, hyperlipidemia, arteriosclerosis involving the endothelial cell which is thought to be an active transport process with potential rate limitations which can possibly be overridden by passive diffusion of L-arginine given in excess. Hence, the rational for combining L-arginine with nitroglycerin for the treatment of nitrate resistance and tolerance. To test this hypothesis, the effects of exposing intact rat aorta to nitroglycerin combined with L-arginine in aqueous solution was studied and the results were compared to the results obtained with SNP combined in an aqueous solution with L-arginine. The effect of combining L-arginine and nitroglycerin appear in FIG. 2. The clinical preparations were as follows:

ANIMAL PREPARATION

Eight Sprague-Dawley rats were used in this nitroglycerin study and two were used in the SNP study. Following removal of the aorta from each rat the aorta was cleaned and cut into 5 segments. The segments were randomly distributed to minimize variation in baseline values. Following this, the segments were incubated in Earl's Salt solution at 37° C.

TREATMENT PROTOCOL

Nitroglycerin Group—one of the five-segments removed served as control to assess the integrity of the endothelium (basal activity). The other four each received 50 μmol of L-arginine. After 30 minutes 1 ml of IBMAX (50 μmol) was added to the 5 segments to prevent any further cGMP degradation by phosphodiesterase (IBMAX is isobutyl methyl xanthine). The 5 segments were treated as follows: A—control-basal activity; B is L-arginine group–50 μmol L-arginine added to basal group; C is the nitroglycerin group–5 μmol nitroglycerin in L-arginine 50 μmol; D is nitroglycerin+$N^G$-nitro-L-arginine methyl ester (L-NAME a known inhibitor of NOS function) group–5 μmol nitroglycerin+0.5m mol of L-NAME and L-arginine 50 μmol; and E is the L-NAME group–0.5m mol of L-NAME and L-arginine at 50 μmol. After 50 minutes each of the segments were removed and placed in 500 μL of 0.1 NHCl. They were left for one hour at which time they were removed and weighed.

CYCLIC GMP ASSAY.

For cGMP determination 400 μL of HCl solution remaining after strips were removed and weighed were transferred into gama flow tubes and cyclic GMP was determined by radioimmunoassay.

DATA INTERPRETATION

A. Control—Basal. This represents cGMP activity at baseline that was generated by resting NO sources of soluble guanylate cyclase activation, i.e. baseline.

B. L-arginine Group. This represents cGMP activity generated by L-arginine and EDRF (endogenous or "native" NO production).

C. Nitroglycerin Group. (L-arginine plus nitroglycerin) The cGMP activity represents the sum of B (L-arginine) plus nitroglycerin induction of cNOS and the subsequent EDRF produced in addition to nitric oxide from nitroglycerin by the L-arginine independent pathway (pro-drug effects).

D. L-NAME Group. L-arginine (L-arginine plus nitroglycerin plus L-NAME). Represents cGMP activity from nitroglycerin enzymatic conversion alone since L-NAME used in excess inhibits NOS derived EDRF from all sources.

E. L-arginine+L-NAME—represents cGMP activity due to non-nitric oxide sources activating soluble guanylate cyclase activation and was subtracted from all measurements to eliminate effects of non NO activation of cGMP. (atrial natriuretic factor, etc.)

From this it is apparent that: Total NO from nitroglycerin is C–B; NO from enzymatic degradation of nitroglycerin to NO equals D–E; EDRF (NOS) stimulation from nitroglycerin=(C–B)–(D–E)

SNP GROUP

A second group of two rats was examined, as above, only in this group SNP was substituted in the treatment protocol for nitroglycerin. These results are shown in FIG. 3, A' B' and E' correspond exactly with A, B, and E of FIG. 2. C' is equal to L-arginine at 50 μmol plus 1 μmol SNP and represents cGMP activity from L-arginine stimulation of EDRF production plus any cNOS activation by SNP plus NO from SNP by non-enzymatic conversion. It does not appear that SNP requires any sulfhydryl group, but rather that it forms NO and cyanide as a by-product nonenzymatically. D' is SNP+L-NAME– represent cGMP activity generated by non enzymatic conversion of SNP to NO alone, i.e. exogenous or "non-native" NO. Total NO from SNP=C'–B'; Total NO from SNP from non-enzymatic conversion=D'–E'; EDRF from SNP by NOS activation=(C'–B')–(D'–E').

RESULTS

FIGS. 2 and 3 summarizes these results with a bar graph representative of the respective detected picomols of cGMP/ 100 mg wet tissue. Although not shown in FIG. 2, when nitroglycerin and L-NAME were combined in the absence of L-arginine, similar results were obtained regarding cGMP production. In both FIGS. 2 and 3 the bar labelled NOS is the amount of "native" NO produced which is total NO minus the NO produced via the L-arginine independent pathway.

Nitroglycerin resistance—tolerance has frustrated cardiologists and pharmacologists since 1888. (Stewart D. D., 1888, Remarkable Tolerance to Nitroglycerin. Philadelphia Polyclinic. 172–5.) These results support the hypothesis outlined FIG. 1A and FIG. 1B and clarify the mechanism of nitroglycerin tolerance. It is believed that an additional nitroglycerin activation site is cNOS in the endothelial cell. Under conditions leading to tolerance the agonist effect of nitroglycerin on cNOS induction leads to a depletion of L-arginine in the endothelial cell secondary to rate limitations in active L-arginine transport pump kinetics FIG. 1A and FIG. 1B. This creates a supply demand mismatch situation at the membrane uptake step and explains why arginine is rate limiting in a canine model. This may also explain why during administration of nitroglycerin a nitrate free interval is required. It is believed that this is necessary so that the endothelial cells can replete the deficient L-arginine by active transport. By adding L-arginine to nitroglycerin it is believed that EDRF can be generated, and in the process a significant reduction in clinical and mortality endpoints can be obtained relative to using nitroglycerin alone or in combination with SNP or other donors of exogenous NO.

The fact that veins are more sensitive to exogenous NO (and most likely "native" NO also), compared to arteries, explains why at low doses nitroglycerin is principally a venous dilator compared to SNP which is a balanced arterial venous dilator. It explains why at 37 micrograms/hr nitroglycerin becomes arterial because at this level all the EDRF potential is realized and pro-drug conversion of NO takes over as the last source of nitric oxide generated by nitroglycerin. This last source of NO generated from pro-drug conversion is equivalent to NO from SNP and generates a similar arterial effect.

It is possible that EDRF is not identical to NO and is possibly the precursor (L—OH—NO half life of 3–50 seconds) for NO. This would seem to explain failed attempts to substitute SNP for nitroglycerin in clinical situations, such as unstable angina and acute myocardial infarction (Flaherty, J. T., M.D., 1983, Comparison of Intravenous Nitroglycerin and Sodium Nitroprusside in Acute Myocardial Infarction. American Journal of Medicine. 53–60.) since EDRF has better anti-ischemic actions and since EDRF would not be produced using SNP, SNP would not lead to the benefits in mortality potentially realizable with nitroglycerin. Another beneficial effect of EDRF produced by cNOS stimulation with nitroglycerin may result from the ability of EDRF to function as a free radical scavenger relative to exogenous NO. (Zembowicz A., et al., 1991, Nitric Oxide and Another Potent Vasodilator are Formed from $N^G$-hyroxy-L-arginine by Culture Endothelial Cells. Pharmacology. Proc. Natl. Acad. Sci. USA 88:11172–76.) In a reperfusion injury a free radical scavenger (possibly EDRF) is needed to absorb the free radicals which appear to be what is happening with L-arginine and nitroglycerin but not with SNP, a non-native source of NO. This can be explained because one would not expect to see the intermediate EDRF with SNP. Tolerance is established and the beneficial effect of nitroglycerin is lost because there is no longer any EDRF being produced or at least until the rate limiting step is overcome by adding L-arginine substrate. This serves an additional mechanism of benefit from the combination or complex because it relates to the fact that used alone nitroglycerin soon loses its beneficial effect in limiting reperfusion injury with patients who have had recent heart attacks and abrupt restoration of blood flow. The same thing is seen in patients who are undergoing re-establishment of blood flow after coronary bypass operations coming off the bypass pump. This form of reperfusion injury is thought to be mediated by free radical generation of reperfusion and preliminary data especially in cats show that L-arginine administered alone also limits free radical production. Therefore, the combination would be likely to limit reperfusion injury relative to nitroglycerin used alone.

These results indicate the formation of a new drug by combining nitroglycerin with L-arginine in excess so as to take advantage of passive diffusion override mechanism of the endothelial cells membrane transport pump as a treatment for nitroglycerin resistance-tolerance. Such a formulation has applications which include hypertension, hypertensive heart disease, coronary heart disease (angina, myocardial infarction, sudden death), cardiovascular diseases (congestive heart failure, stroke, peripheral vascular disease), cerebrovascular ischemia (TIA), and renovascular ischemia.

Another potential utility of this complex is to independently produce EDRF as seen here in rat aorta and the canine results which will be of great value as a treatment for tolerance of nitroglycerin without additional toxicity or inconvenience in administration of nitroglycerin presently used alone. The method of administration would be unchanged.

It appears as though the L-arginine-nitroglycerin mixture is stimulating cNOS selectively and is not inducing iNOS. This is supported by the following:

1. iNOS induction generally leads to irreversible vascular collapse and death. The classic example being endotoxic shock. This was not seen in the present studies.

2. iNOS induction is associated with a positive feedback mechanism for increasing L-arginine transport into the iNOS endothelial cell. (Lind, D. S., M.D., 1993, Endotoxin Stimulates Arginine Transport in Pulmonary Artery Endothelial Cells. Surgery; 114;2; pp 199–205). Supplementing L-arginine administration would therefore only accelerate the tendency of vascular collapse.

3. In states wherein iNOS induction is not present at baseline, the administration of nitroglycerin, L-arginine, alone or combined, does not lead to irreversible vascular collapse. Both nitroglycerin alone or the combination produce dose dependent hypotension which is reversible upon the discontinuation of the exposure to the respective drugs Regarding paragraph 2 above, in states of iNOS induction described above, it is believed that the development of nitroglycerin tolerance may be an opposite effect of nitroglycerin on the membrane pump, i.e a negative feedback mechanism on the active L-arginine membrane transport. This may be a factor which leads to the development of tolerance.

Regarding paragraph 3 above, iNOS induction may be a common feature of all vascular shock, including hemorrhagic and cardiogenic shock. Advanced stages of congestive heart failure with low output syndrome (borderline cardiogenic shock) may likewise be associated with cytokine production (Tumor Necrosis Factor) and induction of iNOS. Care will need to be employed in the future with administration of L-arginine in combination with nitroglycerin in these states much in the same way care is currently employed when administering nitroglycerin alone when patients are hypotensive at baseline.

An eight hour infusion in a normal human volunteer has been performed using a wide range of nitroglycerin concentrations ranging from 12.5 mg/250 cc total volume through 100 mg/250 cc total volume 10% L-arginine and found most importantly the absence of tachycardia previously reported with either L-arginine or nitroglycerin alone. In addition with 2½× times the currently approved dosages of L-arginine exposure (75 g total) there was no evidence of metabolic acidosis from the HCL present in the L-arginine formulation currently approved. This study is summarized below.

EXAMPLE 2

The following study is a normal human volunteer dose ranging study for intravenous nitroglycerin combined with L-arginine. The objective of this study was to examine the combined administration of intravenous nitroglycerin with L-arginine 10% (aqueous) for the following:

1. Reflex tachycardia (baroreceptor reflex activation).
2. Hypotensive activity (therapeutic effect).
3. Metabolic disturbances-metabolic acidosis.
4. Electrocardiographic abnormalities with prolonged infusion.

The patient studied in this dose ranging study was a 47 year old normotensive white male with no prior history of illness or hospitalization and on no chronic medications.

The materials utilized in this study consisted of the following:

1. Tridil brand of intravenous nitroglycerin (5 mg per cc).
2. 10% L-arginine in water (R-Gene™-KABI).
3. Normal saline.
4. 5×150 cc vacuum sealed sterile bottles.
5. Two Ivac Pumps to include a 3 way stopcock for alternating infusions of drug and saline.
6. One Propac cardiac monitor.
7. One Spacelabs 2000 24 hour blood pressure monitor.
8. One Cardionostics Dural-Lite model #2011 holter recorder.

Patient preparation consisted of pretreatment with 40 mg of Pepcid (famotidine-MERCK) and 50 mg of benadryl the night before. 50 mg of benadryl was repeated on the morning of the study. This was done for the purpose of blocking $H_1$ and $H_2$ receptors from any possible activation by L-arginine.

On the morning of the study a baseline EKG was obtained along with Serum Chemistries and Complete Blood Count (CBC). Following this the 24 hour holter monitor, ambulatory blood pressure monitor, and Propac were attached. The blood pressure monitor was calibrated against the Propac and a discrepancy of approximately 20 mmHg of systolic and 10 mmHg of diastolic blood pressure was observed in the left verses right arms respectively. Next, an IV was established in the left foot in the left saphenous vein with an 18 gauge angiocath. An initial maintenance infusion with saline was begun at KVO (keep vein open) rate. Following this six rapid dose response titrations were performed over the following 8 hours and are shown in FIG. 4 with ¼ (bottle #1), ½ (bottle #2), and full strength nitroglycerin in 10% L-arginine (bottle #3). This was followed by a full strength nitroglycerin infusion in water without L-arginine (bottle #4). Next an infusion of pure L-arginine 10% was administered without nitroglycerin in 10% L-arginine (bottle #5). Lastly an infusion consisting of double strength nitroglycerin in 10% L-arginine (bottle #6) was administered. Full strength nitroglycerin was defined as 50 mg of nitroglycerin in a total volume of 250 cc of L-arginine 10% in water or water alone (bottle #4).

With each infusion, the initial rate was 25 cc per hour. Following this the infusion was doubled to 50 cc per hour. This was increased by 50 cc per hour every 5 to 10 minutes until a total infusion rate of 300 cc per hour was achieved. During these infusions blood pressure and heart rate data were recorded every 2 minutes by Propac before increasing the rate of infusion as described above. During bottle changes the infusion was changed to normal saline at 100 cc per hour. At the beginning of each infusion an estimated 10 cc of "dead space" was eliminated from the infusate left over from the previous bottle by running the first 10 cc at a "wide open" rate. Then the 25 cc sequence was re-initiated as previously described above.

Following the final infusion a repeat of Serum Chemistries, CBC, and EKG were obtained.

For each infusion systolic and diastolic right arm blood pressures were averaged. Heart rate was likewise averaged. These averages were obtained by taking each individual reading obtained every two minutes, totaling them, and dividing the period in which the infusion occurred (measurements in between infusions during bottle changes not included).

The results are summarized in FIG. 4. In FIG. 4 SBP means Systolic Blood Pressure, DBP means Diastolic Blood Pressure and HR means Heart Rate. There does not appear to be any evidence of reflex tachycardia with the ratio of nitroglycerin to L-arginine used in FIG. 4. There was a dose dependent blood pressure reduction along with a trend toward dependency on nitroglycerin concentration. There was no evidence of metabolic acidosis developing secondary to L-arginine infused for a prolonged period to the total dose of 75 grams administered over 8 hours. There was no evidence of arrhythmia. There was no evidence of electrocardiographic abnormalities. Clearly, this indicates that the administration of the combined L-arginine/nitroglycerin does not have the adverse consequences seen with either L-arginine or nitroglycerin when administered alone.

The foregoing description of the invention is illustrative of the preferred embodiments of the invention currently contemplated by the inventor thereof. However, it should be clear that the foregoing description of the invention is not to be interpreted in a limitative manner, there being several equivalent systems and manners of performing the present invention. For example, the L-arginine is contemplated to be derived from commercially available products such as R-Gene™ or any other source of pharmaceutical grade L-arginine, and the nitroglycerin can be obtained from a variety of delivery systems well known in the art for nitroglycerine alone, for example: lingual aerosols such as Nitrolingual™ spray 0.4 mg/metered dose from Poulenc Rorer); transdermal systems such as Minitran™ (0.6 mg/hour from 3M); topical ointments such as Nitro-Bid™ Ointment (2% from Marion Merrell Dow as well as tablet and patch form (currently using commercial patch product called Tridil™ from Du Pont). This list is not all inclusive, but is merely meant as a representation of the variety of nitroglycerin delivery systems which could be easily modified to be a delivery system for the combination of L-arginine and nitroglycerin. All that is required is compatible systems for the simultaneous delivery of nitroglycerine and L-arginine. Such a selection of delivery systems and commercial starting materials does not depart from the scope and spirit of the present invention. Hence, the true scope of the invention is only to be defined by the claims appended hereto.

What is claimed is:

1. A method of treating a disease condition in a subject by vasodilation or vasorelaxation comprising:

selecting a subject;

mixing L-arginine and a venous dilator, said venous dilator being different than L-arginine;

administering to said subject a formulation comprising said mixture;

obtaining periodic indicators of vasorelaxations for the subject; and;

continuing administration of the formulation until a desirable state of vasorelaxtion is obtained.

2. The method of claim 1, wherein the formulation is administered intravenously, buccal, intracoronary, intramuscularly, topically, intranasally, rectally, sublingually, orally, subcutaneously, or by patch.

3. The method of claim 1, wherein said disease is hypertension, hypertensive heart disease, coronary heart disease, cardiovascular disease, cerebrovascular disease, and renovascular ischemia.

4. The method of claim 3, wherein said venous dilator is an exogenous source of nitric oxide.

5. The method of claim 4, wherein said exogenous source of nitric oxide is nitroglycerin.

6. The method of claim 4, wherein said exogenous source of nitric oxide is selected from the group consisting of sodium nitroprusside, nitrate esters, isoamylynitrite, SIN-1, cysteine, dithiothreitol, N-acetylcysteine, mercaptosuccinic acid, thiosalicylic acid, and methylthiosalicylic acid.

7. The method of claim 5, wherein L-arginine and nitroglycerin are administered at a therapuetic concentration.

8. The method of claim 7, wherein the therapuetic concentration of L-arginine is from 7.5% to about 30% w/v (g/ml).

9. The method of claim 7, wherein the therapuetic concentration of L-arginine is from 10% to about 15% w/v (g/ml).

10. The method of claim 7, wherein the therapuetic concentration of L-arginine is 10% w/v (g/ml).

11. The method of claim 7, wherein the therapeutic concentration of nitroglycerin is from about 0.2 µg/kg/minute to about 5 µg/kg/minute.

12. The method of claim 7, wherein the therapeutic concentration of nitroglycerin is from about 0.5 µg/kg/minute to about 3 µg/kg/minute.

13. The method of claim 7, wherein the therapeutic concentration of nitroglycerin is from about 0.75 µg/kg/minute to about 2 µg/kg/minute.

14. The method of claim 7, wherein the therapeutic concentration of nitroglycerin is about 1 µg/kg/minute.

15. The method of claim 7, wherein the pH is maintained within the range of 6 to 8.0.

16. The method of claim 7, wherein the pH is maintained within the range of 7 to 7.4.

17. A therapeutic mixture comprising a mixture of L-arginine and an agonist of nitric oxide synthase said agonist being different than L-arginine.

18. The therapeutic mixture of claim 17, wherein the agonist is nitroglycerin.

19. The therapeutic mixture of claim 17, wherein the agonist is further comprised of a receptor mediated agonist selected from the group consisting of:

acetylcholine, substance P, Histamine, arginine vasopressin, bradykinin, Adenosine Triphosphate, Prostaglandin $F_{2a}$, Oxytocin, Endothelium B, and the calcium ionophore A23187.

20. A method of stimulating nitric oxide synthase to produce nitric oxide, said method comprising:

mixing L-arginine and an agonist of nitric oxide synthase said agonist being different than L-arginine;

administering the mixture to a subject having a nitric oxide synthase receptor site; and;

stimulating said nitric oxide synthase to a desirable level.

21. The method of claim 20, wherein said L-arginine is in excess to said agonist.

22. The method of claim 20, wherein the agonist is nitroglycerin.

* * * * *